United States Patent
Hino et al.

(10) Patent No.: US 11,125,721 B2
(45) Date of Patent: Sep. 21, 2021

(54) METHOD FOR MEASURING MAGNETIC TRANSFORMATION RATE OF STEEL SHEET IN ANNEALING FURNACE, APPARATUS FOR MEASURING THE SAME, CONTINUOUS ANNEALING PROCESS, AND CONTINUOUS GALVANIZING PROCESS

(71) Applicant: JFE Steel Corporation, Tokyo (JP)

(72) Inventors: Yoshimichi Hino, Tokyo (JP); Hirokazu Sugihara, Tokyo (JP)

(73) Assignee: JFE Steel Corporation, Tokyo (JP)

( * ) Notice: Subject to any disclaimer, the term of this patent is extended or adjusted under 35 U.S.C. 154(b) by 162 days.

(21) Appl. No.: 16/626,054

(22) PCT Filed: May 23, 2018

(86) PCT No.: PCT/JP2018/019735
§ 371 (c)(1),
(2) Date: Dec. 23, 2019

(87) PCT Pub. No.: WO2019/003727
PCT Pub. Date: Jan. 3, 2019

(65) Prior Publication Data
US 2021/0148859 A1 May 20, 2021

(30) Foreign Application Priority Data
Jun. 28, 2017 (JP) .............................. JP2017-125975

(51) Int. Cl.
*G01N 27/72* (2006.01)
*C21D 9/46* (2006.01)
*G01N 33/20* (2019.01)

(52) U.S. Cl.
CPC ............... *G01N 27/72* (2013.01); *C21D 9/46* (2013.01); *G01N 33/20* (2013.01)

(58) Field of Classification Search
CPC ........ G01N 1/00; G01N 2201/00; G01R 1/00; H01F 1/00
See application file for complete search history.

(56) References Cited

U.S. PATENT DOCUMENTS

| 4,648,916 A | 3/1987 | Morita et al. |
| 4,740,747 A | 4/1988 | Kawashima et al. |
| (Continued) | | |

FOREIGN PATENT DOCUMENTS

| EP | 1308721 A1 | 5/2003 |
| EP | 1503170 A1 | 2/2005 |
| (Continued) | | |

OTHER PUBLICATIONS

Extended European Search Report for European Application No. 18 823 636.8, dated Mar. 10, 2020, 7 pages.

(Continued)

*Primary Examiner* — Jermele M Hollington
*Assistant Examiner* — Temilade S Rhodes-Vivour
(74) *Attorney, Agent, or Firm* — RatnerPrestia (57) ABSTRACT

Provided are a method for measuring the magnetic transformation rate of a steel sheet in an annealing furnace and an apparatus for measuring the same, and a continuous annealing process and a continuous galvanizing process which utilize the method and the apparatus. One such method includes delivering an alternating-current driving signal to the surface of the steel sheet by using an air-core driving coil having a size larger than, a width of the steel sheet, measuring the driving signal reflected by the steel sheet by using air-core receiving coils having a size larger than the width of the steel sheet, and determining the magnetic transformation rate of the steel sheet by using a measurement processing unit based on a distance between the steel sheet and the driving coil which has been corrected by using the measured (Continued)

values of the driving signal obtained by using the receiving coils.

19 Claims, 3 Drawing Sheets

(56) References Cited

U.S. PATENT DOCUMENTS

| | | | |
|---|---|---|---|
| 5,453,689 A | 9/1995 | Goldfine et al. | |
| 6,686,735 B2 | 2/2004 | Daalmans et al. | |
| 2011/0148405 A1* | 6/2011 | Kato | G01R 33/04 324/239 |
| 2014/0055130 A1* | 2/2014 | Nakamura | G01N 27/90 324/240 |
| 2015/0123666 A1 | 5/2015 | Leppanen et al. | |
| 2015/0300989 A1 | 10/2015 | Masleid et al. | |
| 2016/0011282 A1* | 1/2016 | Higaki | G01N 27/9026 324/205 |

FOREIGN PATENT DOCUMENTS

| | | |
|---|---|---|
| JP | 5682443 A | 7/1981 |
| JP | 59109859 A | 12/1982 |
| JP | 59188508 A | 10/1984 |
| JP | 59231446 A | 12/1984 |
| JP | 6269160 A | 3/1987 |
| JP | 10130742 A | 5/1998 |
| JP | 2002039997 A | 2/2002 |
| JP | 2005257701 A | 9/2005 |
| JP | 2012184931 A | 9/2012 |
| JP | 2012201956 A | 10/2012 |
| JP | 2015516086 A | 6/2015 |
| JP | 2016506502 A | 3/2016 |
| KR | 20060001144 A | 1/2006 |
| WO | 03091657 A1 | 11/2003 |

OTHER PUBLICATIONS

Korean Grant of Patent for Korean Application No. 10-2019-7037613, dated May 31, 2021, with translation, 2 pages.
International Search Report and Written Opinion for International Application No. PCT/JP2018/019735, dated Aug. 7, 2018, 5 pages.

* cited by examiner

$I = I0 \cos \omega t$ $V = V0 \cos \omega t + V90 \sin \omega t$

METHOD FOR MEASURING MAGNETIC TRANSFORMATION RATE OF STEEL SHEET IN ANNEALING FURNACE, APPARATUS FOR MEASURING THE SAME, CONTINUOUS ANNEALING PROCESS, AND CONTINUOUS GALVANIZING PROCESS

CROSS REFERENCE TO RELATED APPLICATIONS

This is the U.S. National Phase application of PCT/JP2018/019735, filed May 23, 2018 which claims priority to Japanese Patent Application No. 2017-125975, filed Jun. 28, 2017, the disclosures of these applications being incorporated herein by reference in their entireties for all purposes.

FIELD OF THE INVENTION

The present invention relates to the measurement of the magnetic transformation rate of a steel sheet in a continuous annealing furnace, and in particular, to a method for measuring the magnetic transformation rate of a steel sheet and an apparatus for measuring the magnetic transformation rate of a steel sheet. In addition, the present invention relates to a continuous annealing process and a continuous galvanizing process which utilize the method for measuring the magnetic transformation rate and the apparatus for measuring the magnetic transformation rate.

BACKGROUND OF THE INVENTION

Nowadays, there is a strong need to provide a steel sheet having high strength and excellent workability from the viewpoint of reducing the weight of an automotive steel sheet. To obtain a steel sheet having high strength and high workability, cooling is performed when the steel sheet is in a state in which the ratio of the amount of a γ phase (austenite phase) and an α phase (ferrite phase) has a specific value. Therefore, assessing the ratio of the amount of the above-mentioned each phase at a cooling start temperature is effective for achieving appropriate properties of the steel sheet.

Conventional examples of a method for assessing the ratio of the amount of the above-mentioned each phase include one utilizing a magnetic detector, that is, an apparatus with which the magnetic transformation rate of a steel sheet is measured (refer to Patent Literature 1 and Patent Literature 2). Patent Literature 1 discloses an example of an apparatus for measuring a magnetic transformation rate, that is, an apparatus having a driving coil, which generates a magnetic flux, and a detecting coil, which measures a magnetic flux passing through a steel sheet. Patent Literature 2 discloses another example of an apparatus for measuring a magnetic transformation rate, that is, an apparatus having a driving coil, which generates a magnetic flux, and a detecting coil, which measures a magnetic flux reflected by a steel sheet.

PATENT LITERATURE

PTL 1: Japanese Unexamined Patent Application Publication No. 56-82443 (pages 1 and 2 and FIG. 1)
PTL 2: Japanese Unexamined Patent Application Publication No. 59-188508 (FIG. 2)

SUMMARY OF THE INVENTION

Measuring the ratio of the amount of an austenite phase and a ferrite phase in steel, that is, a transformation rate in steel is not only effective in a hot rolling process, as in the case of the conventional techniques described above, but also important in an annealing process for a high-strength cold-rolled steel sheet. It is possible to use the similar method as used in a hot rolling process also in an annealing process for a high-strength cold-rolled steel sheet as a method for measuring a transformation rate.

However, in the case of the measuring method which utilizes the measuring apparatus described in Patent Literature 1, as described on page 6 of Patent Literature 2, there is a problem in that it is necessary to decrease the distance between a steel sheet and the measuring apparatus to optimize the penetration depth of a magnetic flux into a magnetic material. Therefore, in the case where the measuring apparatus described in Patent Literature 1 is used in an annealing process for a high-strength cold-rolled steel sheet, it is necessary to arrange the measuring apparatus close to the steel sheet in the annealing furnace in which annealing is performed at a temperature of about 900° C., and it is not possible to decrease the distance between the steel sheet and the measuring apparatus in consideration of cooling the measuring apparatus.

On the other hand, in the case of the measuring method which utilizes the measuring apparatus (detecting apparatus) described in Patent Literature 2, since an exciting coil (driving coil) and a detecting coil are arranged on one side of steel, the above-described problem regarding arrangement is solved. However, in the case where a steel sheet repeatedly moves in the up-down direction in, for example, a vertical annealing furnace, it is necessary to arrange the measuring apparatus at an intermediate position in the height direction of the furnace. In this case, to support the measuring apparatus, which has heavy iron cores, in the high-temperature annealing furnace, it is necessary to use members having a large cross-sectional area. Therefore, there is a problem in that the members having a large cross-sectional area, which are used to support the measuring apparatus, hinder the heating and cooling of the annealing furnace.

In addition, since all of the measuring apparatuses described in Patent Literature 1 and Patent Literature 2 are small, it is possible to measure a transformation rate in only part of a steel sheet. Therefore, there is a problem in that it is necessary to arrange many measuring apparatuses in the width direction of a steel sheet to measure a transformation rate across the full width of a steel sheet.

Moreover, in the case of manufacturing a high-strength steel sheet nowadays, the austenite phase fraction is large. However, since the heating efficiency of a solenoid-type induction heating apparatus, which is used for reheating performed in a continuous annealing furnace or reheating performed for alloying zinc in a continuous galvanizing line, is low, the induction heating apparatus is operated at a high output power, which results in unstable temperature control due to an unintended variation in the austenite phase fraction of the steel sheet. In particular, in the case where there is a variation in the austenite phase fraction of a steel sheet, since an electromotive force is generated in the solenoid-type induction heating apparatus due to a variation in the magnetism of the steel sheet, there is a problem in that it is not possible to control the apparatus due to a rapid variation in voltage in the circuit. Since a variation in voltage occurs due to a portion in which there is a variation in the austenite phase fraction entering the solenoid-type induction heating apparatus, it is not possible to predict the occurrence in advance, and it is difficult to perform control to inhibit a variation in voltage which has occurred.

Aspects of the present invention have been completed in view of the situation described above, and an object according to aspects of the present invention is to provide a method for measuring the magnetic transformation rate of a steel sheet in a continuous annealing furnace and an apparatus for measuring the magnetic transformation rate of a steel sheet in a continuous annealing furnace, and a continuous annealing process and a continuous galvanizing process which utilize the method for measuring the magnetic transformation rate and the apparatus for measuring the magnetic transformation rate.

The present inventors diligently conducted investigations to solve the problems described above and, as a result, obtained the following knowledge.

Aspects of the present invention include a method for measuring magnetic transformation of a steel sheet in which the magnetic transformation rate of a steel sheet is measured by arranging a driving coil and receiving coils on one surface side of a steel sheet in an annealing furnace, where the coils are air-core coils having loop paths across the full width of the steel sheet, by delivering an alternating-current driving signal from the driving coil, and by measuring waves reflected by the steel sheet by using the receiving coils.

In the case where a reflected wave is used in accordance with aspects of the present invention, two receiving coils are paired, arranged on both side of the driving coil symmetrically with respect to the driving coil, and connected with phases opposite to each other, so that it is possible to easily recognize a variation in signal due to a variation in the magnetism of a steel sheet. Moreover, in the case where two pairs, where each pair consists of the two receiving coils as described above, are used, by arranging the coils so that the distance of one pair from the driving coil is different from the distance of the other pair from the driving coil, and by using the distances of the receiving coils from the steel sheet calculated from the received and measured values of the driving signal obtained by using the two pairs of the receiving coils, the signal of a magnetic transformation rate is corrected.

In addition, in accordance with aspects of the present invention, by extracting a signal component having a phase difference of 90° with respect to the delivered driving signal from the measured value of the driving signal obtained by using the receiving coil, and by using the signal component having a phase difference of 90°, a transformation rate is determined. Moreover, in accordance with aspects of the present invention, by separating the measured value of the driving signal obtained by using the receiving coil into a signal component having a phase difference of 0° with respect to the delivered driving signal and a signal component having a phase difference of 90° with respect to the delivered driving signal, and by using the ratio of the magnitude of one of the separated signal components to the magnitude of the other, a transformation rate is determined.

In addition, aspects of the present invention include an apparatus for measuring the magnetic transformation of a steel sheet characterized by having a driving coil and receiving coils arranged in an annealing furnace, where the coils form large-area closed circuits across the full width of the steel sheet, and where the coils have no core material.

In addition, aspects of the present invention include a continuous annealing process and a galvanizing process in which, by performing the measurement of magnetic transformation before induction heating is performed, feedforward control is performed in consideration of an effect caused by magnetization of a steel sheet.

Aspects of the present invention have been completed on the basis of the knowledge described above, and are as follows.

[1] A method for measuring a magnetic transformation rate of a steel sheet in an annealing furnace before the steel sheet is subjected to a heating treatment in the annealing furnace, by using a driving coil and receiving coils arranged on one surface side of the steel sheet so that the receiving coils are arranged on both sides of the driving coil and parallel to a surface of the steel sheet, the method including delivering an alternating-current driving signal to the surface of the steel sheet by using an air-core driving coil having a size larger than a width of the steel sheet, measuring the driving signal reflected by the steel sheet by using air-core receiving coils having a size larger than the width of the steel sheet, and determining the magnetic transformation rate of the steel sheet by using a measurement processing unit based on a distance between the steel sheet and the driving coil which has been corrected by using the measured values of the driving signal obtained by using the receiving coils.

[2] The method for measuring a magnetic transformation rate of a steel sheet in an annealing furnace according to item [1], in which two of the receiving coils are paired, arranged symmetrically with respect to the driving coil, connected with phases opposite to each other, and used to measure the reflected driving signal.

[3] The method for measuring a magnetic transformation rate of a steel sheet in an annealing furnace according to item [1] or [2], in which two pairs of receiving coils, where each pair consists of two of the receiving coils connected with phases opposite to each other, are used and arranged so that a distance of one pair from the driving coil is different from a distance of another pair from the driving coil, and in which, by using the measurement processing unit, the magnetic transformation rate is corrected based on the distances of the receiving coils from the steel sheet calculated based on the measured values of the driving signal obtained by using the two pairs of receiving coils.

[4] A method for measuring a magnetic transformation rate of a steel sheet in an annealing furnace before the steel sheet is subjected to a heating treatment in the annealing furnace, by using a driving coil and receiving coils arranged on one surface side of the steel sheet so that the receiving coils are arranged on both sides of the driving coil and parallel to a surface of the steel sheet, the method including delivering an alternating-current driving signal to the surface of the steel sheet by using an air-core driving coil having a size larger than a width of the steel sheet, measuring the driving signal reflected by the steel sheet by using air-core receiving coils having a size larger than the width of the steel sheet, and determining the magnetic transformation rate of the steel sheet by using a measurement processing unit based on a signal component having a phase difference of 90° with respect to the delivered driving signal extracted from the measured values of the driving signal obtained by using the receiving coils.

[5] The method for measuring a magnetic transformation rate of a steel sheet in an annealing furnace according to item [4], in which, in the measurement processing unit, each of the measured values of the driving signal obtained by using the receiving coils is separated into a signal component having a phase difference of 0° with respect to the delivered driving signal and a signal component having a phase difference of 90° with respect to the delivered driving signal, and the magnetic transformation rate is determined based on a ratio of a magnitude of the signal component having a phase difference of 90° to a magnitude of the signal component having a phase difference of 0°.

[6] An apparatus for measuring a magnetic transformation rate of a steel sheet in an annealing furnace before the steel sheet is subjected to a heating treatment in the annealing furnace, by using a driving coil and receiving coils arranged on one surface side of the steel sheet so that the receiving coils are arranged on both sides of the driving coil and parallel to a surface of the steel sheet, the apparatus including an air-core driving coil which forms a large-area closed circuit having a size larger than a width of the steel sheet and delivers an alternating-current driving signal to a surface of the steel sheet, air-core receiving coils which form large-area closed circuits having a size larger than the width of the steel sheet and receive and measure the driving signal reflected by the steel sheet, and a measurement processing unit which determines the magnetic transformation rate of the steel sheet based on a distance between the steel sheet and the driving coil which has been corrected by using the measured values of the driving signal obtained by using the receiving coils.

[7] The apparatus for measuring a magnetic transformation rate of a steel sheet in an annealing furnace according to item [6], in which two of the receiving coils are paired, arranged symmetrically with respect to the driving coil, and connected with phases opposite to each other.

[8] The apparatus for measuring a magnetic transformation rate of a steel sheet in an annealing furnace according to item [6] or [7], in which two pairs of receiving coils, where each pair consists of two of the receiving coils connected with phases opposite to each other, are used and arranged so that a distance of one pair from the driving coil is different from a distance of another pair from the driving coil.

[9] The apparatus for measuring a magnetic transformation rate of a steel sheet in an annealing furnace according to any one of items [6] to [8], in which a number of turns in a coil varies from one receiving coil to another in the receiving coils, and a distance between each of the receiving coils and the driving coil is determined in accordance with the number of turns of the receiving coil.

[10] An apparatus for measuring a magnetic transformation rate of a steel sheet in an annealing furnace in which the magnetic transformation rate of a steel sheet is measured, before the steel sheet is subjected to a heating treatment in the annealing furnace, by using a driving coil and receiving coils arranged on one surface side of the steel sheet so that the receiving coils are arranged on both sides of the driving coil and parallel to a surface of the steel sheet, the apparatus including an air-core driving coil which forms a large-area closed circuit having a size larger than a width of the steel sheet and delivers an alternating-current driving signal to the surface of the steel sheet, air-core receiving coils which form large-area closed circuits having a size larger than a width of the steel sheet and receive and measure the driving signal reflected by the steel sheet, and a measurement processing unit which determines the magnetic transformation rate of the steel sheet based on a signal component having a phase difference of 0° with respect to the delivered driving signal and/or a signal component having a phase difference of 90° with respect to the delivered driving signal which are extracted from the measured values of the driving signal obtained by using the receiving coils.

[11] A continuous annealing process including measuring a magnetic transformation rate of a steel sheet before the steel sheet enters an induction heating apparatus in an annealing furnace by using the method for measuring a magnetic transformation rate of a steel sheet in an annealing furnace according to any one of items [1] to [5] and controlling the induction heating apparatus through feedforward control based on the measured magnetic transformation rate by using the measurement processing unit.

[12] A continuous galvanizing process including measuring a magnetic transformation rate of a steel sheet before the steel sheet enters an induction heating apparatus in an annealing furnace by using the method for measuring a magnetic transformation rate of a steel sheet in an annealing furnace according to any one of items [1] to [5] and controlling the induction heating apparatus through feedforward control based on the measured magnetic transformation rate by using the measurement processing unit.

According to aspects of the present invention, since air-core coils having no iron core and having a size larger than the width of a steel sheet are used, the coils are light and excellent in terms of durability, and it is possible to measure an average transformation rate in the width direction of the steel sheet. In addition, since the distance between the measuring apparatus and a steel sheet is corrected based on the signals obtained by using the receiving coils, and since a magnetic transformation rate is determined based on the corrected distance, there is an improvement in the measurement accuracy of a magnetic transformation rate. In addition, by using aspects of the present invention in a continuous annealing process or a galvanizing process, it is possible to stably control induction heating through feedforward control, even in the case where there is a variation in magnetic transformation rate.

DETAILED DESCRIPTION OF EMBODIMENTS OF THE INVENTION

Hereafter, the embodiments of the present invention will be described. Here, the present invention is not limited to the embodiments below.

Figure 1:
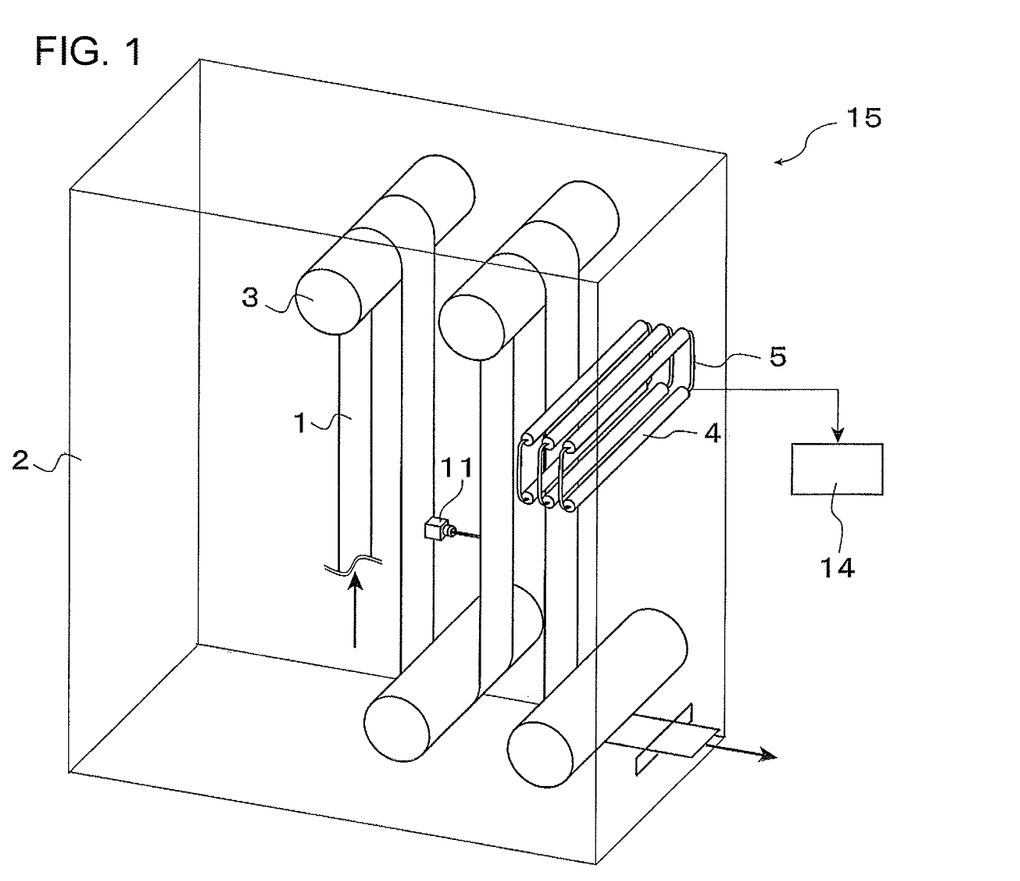
FIG. 1 is a schematic perspective diagram illustrating an apparatus for measuring the magnetic transformation rate of a steel sheet in an annealing furnace according to aspects of the present invention.
Figure 2:
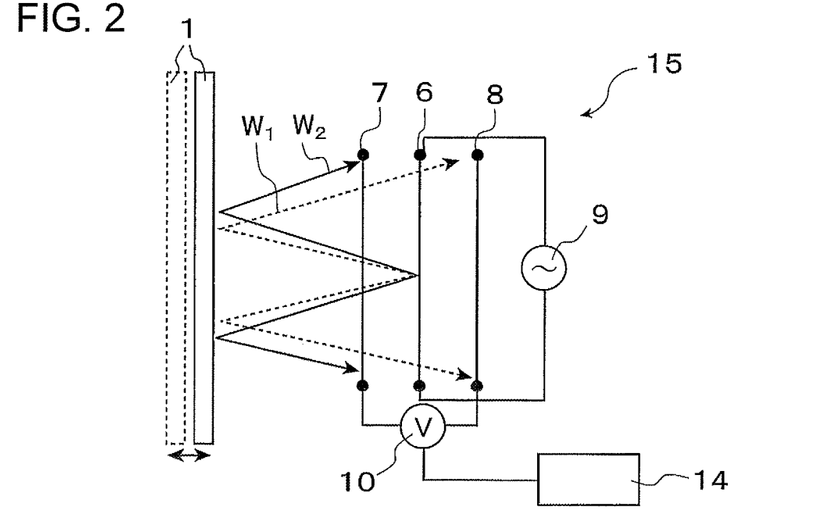
FIG. 2 is a diagram illustrating the principle of a method for measuring a magnetic transformation rate by using the apparatus for measuring the magnetic transformation rate illustrated in FIG. 1.

First, with reference to FIG. 1 and FIG. 2, an apparatus for measuring the magnetic transformation rate of a steel sheet in an annealing furnace and the principle of a method for measuring a magnetic transformation rate which are used in accordance with aspects of the present invention will be described. FIG. 1 is a schematic perspective diagram illustrating the apparatus 15 for measuring the magnetic transformation of a steel sheet in an annealing furnace 2 according to aspects of the present invention. FIG. 2 is a diagram illustrating the principle of the method for measuring a magnetic transformation rate by using the apparatus 15 for measuring magnetic transformation of a steel sheet illustrated in FIG. 1.

As illustrated in FIG. 1, the apparatus 15 for measuring magnetic transformation placed in the annealing furnace 2 has coils 5, a transmitter 9 (not illustrated), a voltmeter 10 (not illustrated), and a measurement processing unit 14.

The coils 5 include one driving coil (exciting coil) and two or more receiving coils. The driving coil is a coil which delivers an alternating-current electromagnetic wave (driving signal) to the surface of a steel sheet. The receiving coils are coils which receive and measure the driving signal reflected by the steel sheet.

The coils 5 are formed by passing conductive wires through air cores 4, which have no iron core. Two of the receiving coils are paired by winding the conductive wire of one of the two coils in a direction opposite to the direction in which the conductive wire of the other coil is wound. As the air core 4, for example, a ceramic pipe or an alumina pipe is used. The air cores 4 are fitted to the annealing furnace 2 so as to penetrate the furnace body and arranged at predetermined intervals in the moving direction of a steel sheet. In this example, one coil is formed by passing a conductive wire through two ceramic pipes so that the wire passes around in a plane parallel to the steel sheet 1, and three coils are arranged parallel to the surface of a steel sheet 1 at predetermined intervals. One of the coils 5 which is placed in the middle is a driving coil (refer to reference 6 in FIG. 3 described below), and a pair of coils 5, each of which is placed on both sides of the driving coil, are receiving coils (refer to references 7 and 8 in FIG. 3 described below). For example, the two receiving coils and the driving coil are arranged at regular intervals.

Incidentally, the number of turns in a coil may vary from one receiving coil to another, and, in the case of different numbers of turns, the distance of one of the two receiving coils from the driving coil may be different from that of the other. With this, even in the case where the interior space of the annealing furnace 2 is small, it is possible to place the apparatus for measuring without an effect of the space.

Figure 4:
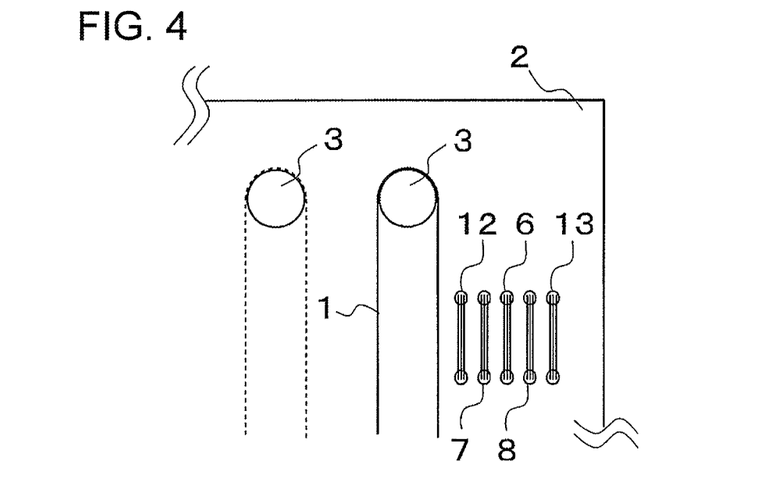
FIG. 4 is a partially enlarged diagram illustrating another example of the present invention.

In addition, in accordance with aspects of the present invention, plural pairs, where each pair consists of two receiving coils, may be used. By arranging plural pairs of receiving coils, there is a further improvement in measurement accuracy. for example, in the case where two pairs of receiving coils are used, as illustrated in FIG. 4, two pairs of receiving coils 7, 8, 12, and 13 are arranged symmetrically with respect to the driving coil 6 so that the distance of one pair from the driving coil is different from the distance of the other pair from the driving coil.

The transmitter 9 is an electric power source which is connected with a coil (driving coil) and which generates a sinusoidal wave having a predetermined frequency and current. Examples of the transmitter include a sinusoidal wave generating device and a function generator.

The voltmeter 10 is connected with a coil (receiving coil) and used to measure the received driving signal obtained by using the receiving coil. Examples of the voltmeter include a lock-in amplifier.

The measurement processing unit 14 is an arithmetic unit which corrects the distance between a steel sheet and the driving coil on the basis of the measured values of the driving signal obtained by using the receiving coils and which determines the magnetic transformation rate of the steel sheet on the basis of the corrected distance. In another case, the measurement processing unit 14 is an arithmetic unit which extracts a signal component having a phase difference of 0° with respect to the delivered driving signal and a signal component having a phase difference of 90° with respect to the delivered driving signal from the measured values of the driving signal obtained by using the receiving coils and which determines the magnetic transformation rate of a steel sheet on the basis of the extracted signal components. That is, the measurement processing unit 14 corrects the distance on the basis of the difference in installation position, the difference in ratio (signal ratio) of the amount of one of the signals to the amount of the other, and a difference in phase angle of the signal between the plural receiving coils. Incidentally, the method for measuring a magnetic transformation rate by using the measurement processing unit 14 is not described here, because it will be described with reference to FIG. 2 below.

Here, the apparatus 15 for measuring magnetic transformation may further have a thermometer 11. In the case where the thermometer is used, since it is possible to use the measured temperature of a steel sheet in the method for measuring a magnetic transformation rate, it is possible to further improve the measurement accuracy. The thermometer 11 is used to measure the surface temperature of the steel sheet 1, and examples of the thermometer 11 include a radiation thermometer.

In the apparatus 15 for measuring magnetic transformation, three coils 5 (one driving coil and two receiving coils) are arranged parallel to the surface of the steel sheet 1, and an unillustrated transmitter is connected to the driving coil and an unillustrated voltmeter is connected to the receiving coils. In the apparatus 15 for measuring magnetic transformation, the electromagnetic wave (signal) delivered by the driving coil is controlled on the basis of input data by using an unillustrated magnetic transformation measurement processing control unit through a controller. When a steel sheet passes in front of the apparatus 15 for measuring magnetic transformation, the driving coil delivers a signal (driving signal) to the steel sheet 1, the receiving coils receive and measure the signal reflected by the steel sheet 1, and the measurement processing unit 14 corrects the distance between the steel sheet and the driving coil on the basis of the measured values of the driving signal obtained by using the receiving coils and determines the magnetic transformation rate of the steel sheet on the basis of the corrected distance. On the other hand, when a steel sheet does not pass in front of the apparatus 15 for measuring magnetic transformation, since the signal delivered by the driving coil is canceled out by the function of the receiving coils connected with phases opposite to each other, no signal is sent to the measurement processing unit 14.

In another case, when a steel sheet passes in front of the apparatus 15 for measuring magnetic transformation, the measurement processing unit 14 extracts a signal component having a phase difference of 0° with respect to the delivered driving signal and a signal component having a phase difference of 90° with respect to the delivered driving signal from the measured values of the driving signal obtained by using the receiving coils and determines the magnetic transformation rate of a steel sheet on the basis of the extracted signal components. On the other hand, when a steel sheet does not pass in front of the apparatus 15 for measuring magnetic transformation, no signal is sent to the measurement processing unit 14 as in the case described above.

Here, in the case where aspects of the present invention are used in a continuous annealing process or a continuous galvanizing process, the magnetic transformation rate of a steel sheet is measured before the steel sheet passes through an induction heating apparatus in an annealing furnace, and the measured magnetic transformation rate is sent to a subsequent induction heating apparatus by using the measurement processing unit 14 to perform feedforward control.

Incidentally, although the driving signal delivered by the driving coil in the apparatus 15 for measuring magnetic transformation described above is basically constant, in the case where the magnitudes of the received signals (that is, measured values of the driving signal) obtained by using the receiving coils is excessively large or excessively small, the magnitude of the signal delivered by the driving coil may be controlled by using the above-mentioned magnetic transformation measurement processing control unit. For example, the magnitude of the signal delivered by the driving coil is changed to 0.1 or 10 times the original magnitude on the basis of whether the received signals obtained by using the receiving coils are in an over-range state or in an under-range state.

According to aspects of the present invention, since the driving coil and the receiving coils used for measuring the magnetic transformation rate of a steel sheet are air-core coils, which have no iron core, having a loop path across the full width of the annealing furnace, the coils are light and excellent in terms of durability. In addition, since the driving coil and the receiving coils check the signals related to the magnetic transformation rate across the full width of a steel sheet, there is an advantage in that it is possible to measure an average transformation rate in the width direction of a steel sheet (that is, an average magnetic transformation rate in the width direction of a steel sheet).

In addition, since two of the receiving coils are paired and connected with phases opposite to each other, noise signals passing through the receiving coils cancel each other out. With this, it is possible to clearly measure the magnetic signal of a steel sheet.

Hereafter, with reference to FIG. 2, the principle of the method for measuring the magnetic transformation rate of a steel sheet in accordance with aspects of the present invention will be described.

The magnetic transformation rate of a steel sheet is measured by using a phenomenon in which the magnetism of a steel sheet changes from paramagnetism to ferromagnetism as an austenite phase transforms into a ferrite phase in the steel.

In accordance with aspects of the present invention, first, the driving coil is controlled by the magnetic transformation measurement processing control unit in the apparatus 15 for measuring a magnetic transformation rate through a controller. Then, the driving coil 6 delivers an electromagnetic wave (driving signal) to the steel sheet 1.

The driving signal is reflected from the surface on the front side of the steel sheet 1 after the driving signal has been subjected to the effect of the whole thickness of the steel sheet 1. The reflected waves $w_2$ and $w_1$ enter the receiving coils 7 and 8 respectively. Since signals are generated due to the reflected waves $w_2$ and $w_1$ in the receiving coils 7 and 8, the magnitudes of the generated signals are measured by using the voltmeter 10.

Subsequently, by using the measurement processing unit 14, the distances of the receiving coils 7 and 8 from the steel sheet 1 are calculated from the difference in magnitude between the reflected waves $w_2$ and $w_1$ obtained by using the receiving coils 7 and 8. Here, as illustrated in FIG. 2, the distances of the receiving coils 7 and 8 from the steel sheet 1 are different from each other, and the receiving coils 7 and 8 are connected with phases opposite to each other. Therefore, signals generated in the receiving coils 7 and 8 cancel each other out. In addition, since noise signals passing through the receiving coils 7 and 8 cancel each other out, it is possible to prevent noise. However, since an electromagnetic wave attenuates by distance, signals generated in the receiving coils 7 and 8 due to the signal delivered by the driving coil 6 do not completely cancel each other out, and only the signals entering from the steel sheet may be obtained.

Therefore, in accordance with aspects of the present invention, by measuring the sum of the signals generated in the receiving coils 7 and 8, and by using only the signal V entering from the steel sheet, the amount of displacement of the steel sheet 1 from a reference position is calculated. Then, the distance between the steel sheet 1 and the apparatus 15 for measuring magnetic transformation is calculated on the basis of the calculated displacement. Here, the term "reference position of a steel sheet" refers to the position of the steel sheet 1 indicated by the dotted line in FIG. 2 and means the position of a steel sheet when the steel sheet is stretched between sheet-passing rolls without loosening. In addition, in FIG. 2, the double-headed arrow indicates the amount of displacement.

Subsequently, by using the measurement processing unit 14, the signal V which has entered the receiving coils 7 and 8 is converted to a corrected signal $V_1$, which is calculated on the assumption that the steel sheet is at the reference position, on the basis of the distances calculated as described above. Then, for example, by comparing a calibration curve for a signal ratio, which has been recorded in advance in a memory part or the like in the apparatus 15 for measuring a magnetic transformation rate, and the corrected signal $V_1$, the magnetic transformation rate of the steel sheet is calculated on the basis of a relationship diagram between the temperature of a steel sheet and phase variation due to a transformation rate. Regarding the calibration curve, it is sufficient that one or more kinds of signal are selected, and the calibration curve be one with which it is possible to determine the distance between a steel sheet and the coil from the signal ratio. For example, in the case where the magnitudes of a signal for a steel sheet having a ferrite phase fraction of 100% and a signal for a steel sheet having an austenite phase fraction of 100%, which are obtained in the case of the standard position of a steel sheet (reference position of a steel sheet), are used, by comparing the magnitudes of such signals with the corrected signal $V_1$, the magnetic transformation rate of the steel sheet is calculated on the basis of a relationship diagram between the temperature of a steel sheet and phase variation due to a transformation rate.

Here, as the temperature of a steel sheet, for example, an estimated value which is calculated by using a control system in a CAL (continuous annealing line) or CGL (continuous galvanizing line) process is used. On the other hand, as described above, the thermometer 11 may be installed in the apparatus 15 for measuring a magnetic transformation rate. In this case, the thermometer 11 is placed so that the temperature of a steel sheet is measured before the steel sheet 1 passes in front of the three coils 5 in the apparatus 15 for measuring magnetic transformation according to aspects of the present invention. Then, by using the measured temperature of the steel sheet and the phase variation (corrected signal $V_1$) calculated by using the measurement processing unit 14, it is possible to calculate the magnetic transformation rate of the steel sheet on the basis of a relationship diagram between the temperature of a steel sheet and phase variation due to a transformation rate, which has been measured in advance and recorded in a memory part or the like in the apparatus 15 for measuring a magnetic transformation rate.

In addition, in accordance with aspects of the present invention, by extracting a signal component (V90°) having a phase difference of 90° with respect to the delivered driving signal (exciting signal) from the above-described signal V (summed signal) entering from the steel sheet, a transformation rate is calculated. This is because the signal component having a phase difference of 90° is based on Faraday's law of induction and represents the magnetism of a steel sheet. By comparing the extracted signal component (V90°) having a phase difference of 90° and a calibration curve for a signal ratio, which has been measured in advance and recorded in a memory part or the like in the apparatus 15 for measuring a magnetic transformation rate, it is possible to calculate the magnetic transformation rate of the steel sheet on the basis of a relationship diagram between the temperature of a steel sheet and phase variation due to a transformation rate. The reason why the phase component is used is as follows. Since there may be a case where signal V entering from one steel sheet varies from one measurement position to another, it is not possible to determine whether a variation in the entering signal is caused by a variation in the magnetism of the steel sheet. Therefore, by extracting a phase component, only a variation in magnetism is focused on. In accordance with aspects of the present invention, the reason why a signal component having a phase difference of 90° is used is because such a component represents the effect of the magnetism of a steel sheet most in the received signal obtained by using the receiving coils.

Moreover, in accordance with aspects of the present invention, a signal component (V0°) having a phase difference of 0° with respect to the delivered driving signal (exciting signal) and a signal component (V90°) having a phase difference of 90° with respect to the delivered driving signal are extracted from the above-described signal V (summed signal) entering from the steel sheet. Then, by calculating the ratio (V90°/V0°) of the extracted signal component (V90°) having a phase difference of 90° to the extracted signal component (V0°) having a phase difference of 0°, the phase angle of the received signal obtained by using the receiving coil with respect to the driving signal (exciting signal) is calculated. By using the calculated phase angle, the magnetic transformation rate of the steel sheet is calculated. Here, the reason why a signal component having a phase difference of 0° is used is because such a component represents mainly the effect of the electric resistance of a steel sheet. The reason why a signal component having a phase difference of 90° is used is because, as described above, such a component represents the effect of the magnetism of a steel sheet most in the received signal V obtained by using the receiving coils 7 and 8. In addition, the reason why the phase angle)) (arctan(V90°/V0°)), which is calculated from V90°/V0°, is used is because such a phase angle is not subjected to the effect of a variation in the magnitude of a signal due to a distance between a steel sheet and a measurement position, that is, variation in the magnitude of the signal of the received driving signal, when a magnetic transformation rate is calculated by utilizing the fact that a phase angle varies depending on the state of a steel sheet to be measured.

Here, although a case where one pair of receiving coils is used has been described, two or more pairs of receiving coils, where each pair consists of two receiving coils, may be used in accordance with aspects of the present invention as described above. In this case, since there is an improvement in the above-described correction accuracy compared with a case where one pair of receiving coil is used, it is possible to obtain a magnetic transformation rate with an improved accuracy. Here, a specific measuring method in the case where two pairs of receiving coils are used is not described, because it will be described in EXAMPLE 2 below.

According to aspects of the present invention, since the driving coil and the receiving coils are placed on one side of the steel sheet, a driving signal, which is an electromagnetic wave (driving signal) delivered from the driving coil and reflected by the steel sheet, is received by the receiving coils. The magnitude of the received signal varies depending on the positions of the receiving coils which are arranged at some distances from the steel sheet. Therefore, by arranging the receiving coils so that the path lengths of the electromagnetic wave for the receiving coils are different from each other, the distances of the receiving coils from the steel sheet are determined on the basis of the difference in the magnitude of the received driving signal between the receiving coils. Subsequently, by correcting the received signals obtained by using the receiving coils on the basis of the determined distances, it is possible to determine a magnetic transformation rate on the basis of the corrected received signals obtained by using the receiving coils. At this time, by using two pairs of receiving coils, where each pair consists of two receiving coils connected with phases opposite to each other, since there is an improvement in correction accuracy, it is possible to obtain clearer signals. As a result, there is an improvement in the measurement accuracy of a magnetic transformation rate.

In addition, the received signals obtained by using the receiving coils represent a mixture of the effect of the magnetism of the steel sheet and the effect of an induced current flowing in the steel sheet. In the case where the driving signal is sinusoidal, the magnitude and phase of the signal vary depending on the temperature and transformation rate of the steel sheet. Therefore, according to aspects of the present invention, a signal component having a phase difference of 90° with respect to the driving signal (exciting signal), which represents the effect of the magnetism of the steel sheet most, is extracted from the sum of the received driving signals obtained by using the receiving coils. By determining a magnetic transformation rate on the basis of the magnitude of the extracted signal component having a phase difference of 90° or the magnitude corrected on the basis of the reference position of the steel sheet, it is possible to determine a magnetic transformation rate with accuracy.

Moreover, according to aspects of the present invention, by separating the received driving signal obtained by using the receiving coils into a signal component having a phase difference of 0° with respect to the driving signal (exciting signal) and a signal component having a phase difference of 90° with respect to the driving signal, the ratio of the magnitude of one of the separated phase components to the magnitude of the other is determined. By calculating the phase angle of the received driving signal with respect to the driving signal (exciting signal) from the determined ratio, it is possible to determine a magnetic transformation rate regardless of the effect of the positions of the steel sheet and the driving coil, or more specifically, regardless of the magnitudes of the signals which vary depending on the distances of the group of the coils (driving coil and receiving coils) from the steel sheet.

As described above, according to aspects of the present invention, since the driving coil and the receiving coils are air-core coils, which have no iron core, it is sufficient that light coils, which are composed only of conductive wires, be arranged across the full width of a continuous annealing furnace. With this, even in an atmosphere furnace, in which heating is performed to a temperature of about 900° C., the coils are not damaged by their weight, and it is possible to stably perform measurement.

In addition, from the viewpoint of the responsiveness and easiness of signal processing, as a signal delivered from the driving coil, a signal having a constant frequency and a constant magnitude, such as a sinusoidal wave, a rectangular wave, or a pulse wave, is used. According to aspects of the present invention, when the driving coil and the receiving coils are arranged on one of the front and back sides of a steel sheet to perform measurement, the number of the receiving coils is set to be two. The two receiving coils are arranged symmetrically with respect to the driving coil and connected with phases opposite to each other. This makes it possible for signals generated in the two receiving coils due to the driving coil to cancel each other out. Also, since this makes it possible for noise signals penetrating the two receiving coils to cancel each other out, it is possible to prevent noise. At this time, the signal delivered by the driving coil is reflected by the steel sheet so as to enter the two receiving coils so that signals are generated. Since distances of the two receiving coils from the steel sheet are different from each other, and since the signals generated in the two receiving coils are different from each other, by measuring the sum of the signals generated in the two receiving coils, which are connected with phases opposite to each other, it is possible to use only the signals entering from the steel sheet.

In addition, according to aspects of the present invention, two pairs, where one pair consists of the two receiving coils connected with phases opposite to each other, may be used and arranged so that the distance of one pair from the driving coil is different from the distance of the other pair from the driving coil. In this case, since the distance of the one pair from the driving coil is different from the distance of the other pair from the driving coil, by using the difference in signal ratio of the signal reflected by the steel sheet (signal entering the receiving coil), it is possible to calculate the displacement of the steel sheet from the reference position. By correcting the effect of the distance from the steel sheet on the magnitude of the received signal obtained by using the receiving coil on the basis of the calculated displacement, it is possible to measure a magnetic transformation rate with increased accuracy compared with a case of one pair of the receiving coils.

The signal, which is delivered from the driving coil and reflected by a steel sheet, is generated by an eddy current generated in the steel sheet, and the magnitude and phase difference with respect to the original signal of the reflected signal vary depending on the magnetism and electric resistance of the steel sheet. In the case of steel in the ferromagnetic phase, the magnetism of the steel sheet has a strong effect on the phase component of the received driving signal obtained by using the receiving coil having a phase difference of 90° with respect to the driving signal. Therefore, in accordance with aspects of the present invention, since the transformation rate of the steel sheet is determined on the basis of the magnitude of the phase component of the measured signal having a signal difference of 90° with respect to the driving signal, it is possible to clearly measure the magnetism of the steel sheet, which results in a magnetic transformation rate being measured with accuracy.

In addition, according to aspects of the present invention, by separating the measured signal into a signal component having a phase difference of 0° with respect to the driving signal and a signal component having a phase difference of 90° with respect to the driving signal, a transformation rate is determined on the basis of the ratio of the magnitude of one of the separated phases to the magnitude of the other or the phase difference of the measured signal with respect to the driving signal. With this, it is possible to measure a magnetic transformation rate with accuracy and with no effect of a variation in the magnitude of the signal due to a variation in the position of the steel sheet.

The apparatus for measuring a magnetic transformation rate and the method for measuring a magnetic transformation rate according to aspects of the present invention described above may be used in a continuous annealing process or a continuous galvanizing process. In this case, by measuring a magnetic transformation rate before a steel sheet enters a solenoid-type induction heating apparatus for reheating in an annealing furnace in a continuous annealing process or in a furnace in a continuous galvanizing process, it is possible to assess the magnetic transformation rate of the steel sheet. With this, by calculating the effect on the induction heating apparatus on the basis of the measurement results of the magnetic transformation rate of the steel sheet in advance, it is possible to perform control to inhibit a variation in voltage from occurring in the induction heating apparatus.

Here, there is no particular limitation on the conditions regarding the temperature or the like applied to, for example, heating, soaking, cooling, and a coating treatment in the continuous annealing process or the continuous galvanizing process according to aspects of the present invention, and known conditions may be applied.

According to aspects of the present invention, it is possible to assess the magnetic transformation rate of a steel sheet in an annealing furnace. With this, it is possible to assess the effect of the magnetic transformation rate on an induction heating apparatus in advance before solenoid-type induction heating is performed in a continuous annealing process or a galvanizing process. In addition, by performing feedforward control on the induction heating apparatus, it is possible to stably perform induction heating, even in the case where there is a variation in magnetic transformation rate.

Figure 3:
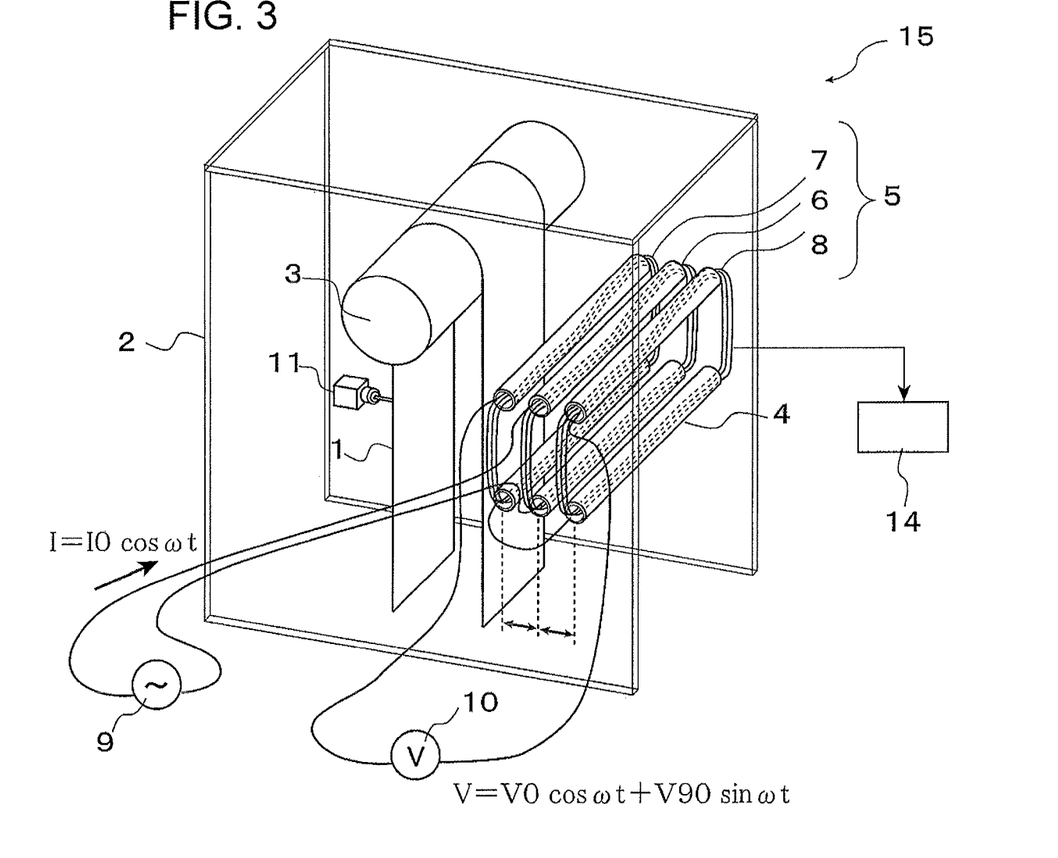
FIG. 3 is a perspective diagram illustrating an example of the present invention.
Figure 5:
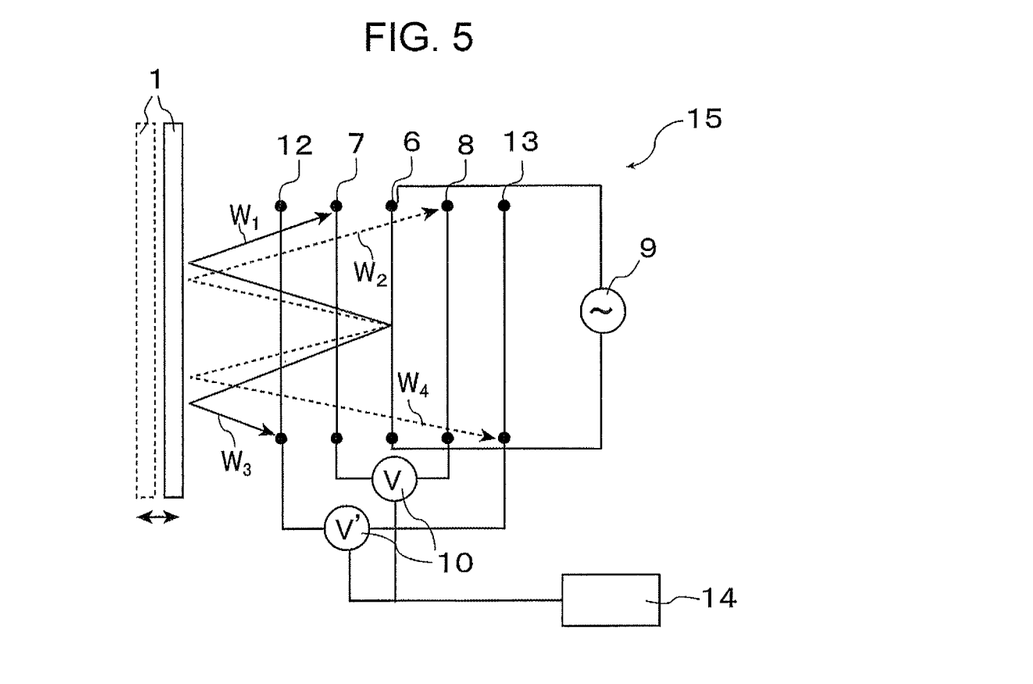
FIG. 5 is a diagram illustrating the principle of a method for measuring a magnetic transformation rate in another example of the present invention.
Figure 6:
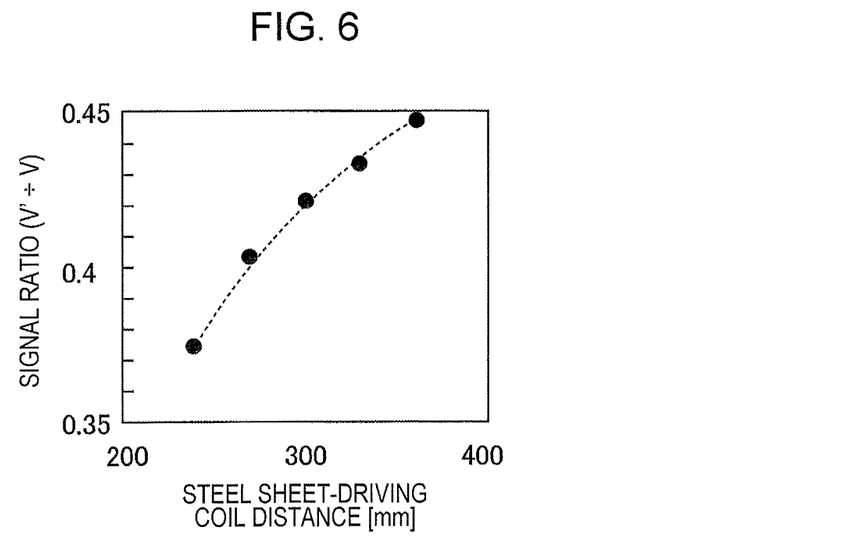
FIG. 6 is a graph illustrating the relationship between the distance (mm) between a steel sheet and a driving coil and a signal ratio (V'/V) in another example of the present invention.

Hereafter, with reference to FIGS. 3 through 6, the present invention will be described in detail in accordance with examples. Here, the present invention is not limited to the examples below. FIG. 3 is a diagram illustrating an example of the present invention, and FIGS. 4 through 6 are diagrams illustrating another example of the present invention.

EXAMPLE 1

As illustrated in FIG. 1 described above, the steel sheet 1 is annealed while the moving direction of the steel sheet is changed by using the hearth rolls 3 in the vertical continuous annealing furnace 2. In this example, after the steel sheet had been subjected to heating to a temperature of 800° C. followed by cooling with a gas jet to a temperature of 600° C., the steel sheet passed through the coils 5 (driving coil 6 and receiving coils 7 and 8) in the apparatus 15 for measuring magnetic transformation according to aspects of the present invention.

Here, in this example, the furnace 2 had a width of 2.5 m, and the steel sheet 1 had a width of 1 m to 1.8 m. In addition, six ceramic pipes 4 were placed so as to penetrate the continuous annealing furnace 2, three coils 5 were formed, where one coil was formed by passing a conductive wire through two ceramic pipes 4 so that the wire went around in a plane parallel to the steel sheet 1. To form one coil loop, two ceramic pipes 4 were arranged so that the distance between the pipes was 0.5 m in the moving direction of the steel sheet. The ceramic pipe 4 had an external diameter of 30 mm, an internal diameter of 24 mm, and a length of 2000 mm, and a copper-alloy conductive wire having a diameter of 2 mmϕ was passed through the pipes with the number of turns of 10. The ceramic pipes 4 each had a weight of about 5 kg. However, since the copper-alloy wire had a very small diameter and low stiffness, the coil might be deflected. In accordance with aspects of the present invention, to inhibit the copper-alloy wire from being deflected, the wire was subjected to tension applied by flanges located on the furnace wall. Like this, since the copper-alloy wire was prevented from touching the internal walls of the ceramic pipes, the coils were stably installed.

In FIG. 3, the apparatus 15 for measuring magnetic transformation in the vertical continuous annealing furnace 2 in an example (hereinafter, referred to as "example 1") of the present invention is illustrated in detail. As illustrated in FIG. 3, the three coils 6, 7, and 8 were arranged parallel to the surface of the steel sheet 1. The coil 6 was a driving coil, and the coils 7 and 8 were receiving coils. The distance of the driving coil from the steel sheet was 200 mm. The driving coil 6 was connected to an electric power source (transmitter) 9, which delivered a sinusoidal wave with a frequency of 55 Hz and a current of 1 A, and functioned as a driving coil. The receiving coil 7 was placed 100 mm closer to the steel sheet 1 than the driving coil 6. On the other hand, the receiving coil 8 was placed farther away from the steel sheet 1 than the driving coil 6 by 100 mm, which is the distance of the receiving coil 7 from the driving coil 6.

The receiving coil 7 and the receiving coil 8 were electrically connected so as to form a pair of receiving coils, in which the conductive wire of one of the two coils was wound in a direction opposite to the direction in which the conductive wire of the other coil was wound, and the magnitudes of the signals (reflected waves) $w_1$ and $w_2$, which were reflected by the steel sheet 1, were measured by using the voltmeter 10. By connecting the two coils of which the conductive wires were wound in directions opposite to each other like this, since signals generated in the receiving coils 7 and 8 due to the receiving coils 7 and 8 receiving an electromagnetic wave (driving signal) delivered by the driving coil 6 cancel each other out, no signal is measured in the case where a steel sheet does not exist. Here, regarding signals generated by background noises, signals generated by the noises passing through the receiving coils 7 and 8 also weaken each other as a result of the conductive wires of the two coils being wound in directions opposite to each other being connected.

On the other hand, in the case where a steel sheet exists, an electromagnetic wave delivered by the driving coil 6 is reflected by the steel sheet 1, which is located 200 mm from the driving coil 6. Then, the reflected wave travels further 100 mm from the steel sheet to reach the receiving coil 7, while the reflected wave travels further 300 mm from the steel sheet to reach the receiving coil 8. At this time, since an electromagnetic wave attenuates by distance, signals generated in the receiving coils 7 and 8 due to the signal delivered by the driving coil 6 do not completely cancel each other out. Therefore, only the signals entering from the steel sheet are obtained.

To increase the effect of such attenuation, the distance in the moving direction of the steel sheet between the two ceramic pipes 4 forming the driving coil 6 should be decreased. However, in the present example 1, the distance in the moving direction of the steel sheet between the pipes was set to be the same in each of the three coils 6, 7, and 8 from the viewpoint of constructability and maintainability.

In addition, in the present example 1, since the receiving coils 7 and 8 had the same number of turns, the distances of the two coils from the driving coil 6 was set to be the same. Here, the numbers of turns of the receiving coils 7 and 8 may be different from each other. The distances of the receiving coils 7 and 8 from the driving coil 6 may be determined in accordance with the respective numbers of turns so that the signals received from the driving coil 6 cancel each other out. With this, even in the case where there is a limitation caused by surrounding conditions on the installation position of the three coils in the apparatus 15 for measuring magnetic transformation, it is possible to install the receiving coils 7 and 8 in accordance with installation conditions.

As described above, the driving coil and the receiving coils according to aspects of the present invention check the signals corresponding to the magnetic transformation rate of the full width of the steel sheet. Therefore, it is possible to measure an average transformation rate in the width direction of the steel sheet (average magnetic transformation rate in the width direction of the steel sheet).

In the present example 1, the conductive wire of the coil was allowed to repeatedly come out from the furnace body and pass across the full width of the furnace to form a loop path. To decrease the effect of a steel shell, which is a magnetic material, the loop path may be formed inside the steel shell. In the present example 1, since the steel shell was almost homogeneous, the effect of the steel shell was canceled out by the receiving coils 7 and 8 connected with phases opposite to each other, which resulted in no problem. Here, the term "steel shell" means steel plates forming the surface of an annealing furnace.

In the present example 1, as the voltmeter 10, a lock-in amplifier was used. By using the voltmeter 10, a measured signal was separated into a voltage signal V0 having a phase difference of 0° with respect to the phase of the driving current signal and a voltage signal V90 having a phase difference of 90° with respect to the phase of the driving current signal.

In the present example 1, the surface temperature of the steel sheet was measured by using the thermometer 11 placed so that the temperature of the steel sheet was measured before the steel sheet 1 passed in front of the three coils 5 in the apparatus 15 for measuring magnetic transformation according to aspects of the present invention.

By using the temperature of the steel sheet measured as described above and the phase variation calculated by using the measuring processing unit, it is possible to obtain the transformation rate of the steel sheet on the basis of a relationship diagram between the temperature of a steel sheet and phase variation due to a transformation rate, which has been measured in advance and recorded in a memory part or the like in the measurement processing unit. Specifically, by using the lock-in amplifier, the measured voltage (V=V0 cos ωt+V90 sin ωt) was separated into V0 and V90. From these measured values, arctan (V90°/V0°) was calculated, and the calculation result was used for evaluation. Here, in the present example 1, since a phase angle was determined within a tolerance of ±2°, it was possible to measure a transformation rate within a tolerance of ±1%.

Incidentally, when measurement was performed, since the steel sheet 1 slightly vibrated between the hearth rolls 3, there was a variation in the distance between the steel sheet 1 and the three coils 5 in the apparatus 15 for measuring magnetic transformation. Therefore, there was a variation in the signals measured by using the voltmeter 10. In the present example 1, it was possible to stably perform measurement by using an average measured value per 3 seconds.

In contrast, as a comparative example, a type of an apparatus for measuring a transformation quantity which is described in the fourth example (FIG. 7) in Patent Literature 2 (Japanese Unexamined Patent Application Publication No. 59-188508), which was driven at a frequency of 55 Hz, was installed in a vertical continuous heat treatment furnace. In this case, the sensing unit of the apparatus for measuring a transformation quantity (corresponding to the three coils according to the present example) had an outer size of 80 mm×80 mm×200 mm and a weight of 10 kg. To protect this sensing unit against the heat in the annealing furnace, it is necessary to use a water-cooled protection box (having an outer size of 200 mm×200 mm×500 mm and a total weight of 50 kg), which contains the sensing unit. It was necessary to install this protection box on the top of a supporting post extended from the side wall of the annealing furnace so that the distance between the protection box and the steel sheet was 100 mm. Therefore, for this installation, it was necessary to perform long-term installation work including the reinforcement of the furnace wall.

In addition, in the case of the comparative example, since a structure in which a heavy object was supported by using a supporting post was used, the sensing unit vibrated due to the vibration of, for example, rollers for transporting the steel sheet, and large vibration having an amplitude of about 20 mm and being supposed to be a resonant vibration occurred when the steel sheet was transported at a low speed. Due to this vibration, since crack occurred in the basal portion of the supporting post, the supporting post was broken down in two months.

In the case according to aspects of the present invention described in the example 1, since the three coils 5 in the apparatus 15 for measuring magnetic transformation were formed of light ceramic pipes and conductive wires, no vibration occurred when the steel sheet was transported. As a result, there was no breaking down, even after a long-term operation.

EXAMPLE 2

FIG. 4 is a side view illustrating another example (hereinafter, referred to as "example 2") of the present invention.

As illustrated in FIG. 4, in the present example 2, a pair of receiving coils 12 and 13 are added. Here, the description regarding the configuration other than this is omitted, because the description regarding the configuration other than this is the same as that in example 1.

The receiving coils 12 and 13 were, as in the case described above, connected so that one of the two coils was wound in a direction opposite to the direction in which the other coil was wound. In the receiving coils 12 and 13, the magnitude (voltage V') of the signal received from the driving coil 6 was measured by using an unillustrated voltmeter. In FIG. 4, the distances of the receiving coils 7, 8, 12, and 13 and the driving coil 6 from the steel sheet 1 indicated by the solid line are respectively 200 mm, 400 mm, 100 mm, 500 mm, and 300 mm.

The electromagnetic wave (driving signal) delivered by the driving coil 6 was reflected by the steel sheet 1, and reflected waves $w_1$, $w_2$, $w_3$, and $w_4$ enter the receiving coils 7, 8, 12, and 13 respectively. As illustrated in FIG. 5, the distances of the receiving coils 7, 8, 12, and 13 from the steel sheet 1 were different from each other. In addition, in each of the pair consisting of the receiving coils 7 and 8 and the pair consisting of the receiving coils 12 and 13, the constituent coils were connected so that one of the two coils was wound in a direction opposite to the direction in which the other coil was wound. Therefore, the signal ratio of V' to V, where V' and V were obtained by using respective pairs of the receiving coils, that is, V'/V, varied depending on the position of the steel sheet 1. Here, the expression "depending on the position of the steel sheet 1" means dependence on the distance (mm) between the steel sheet and the driving coil.

In example 2, voltage signals V90 and V90' having a phase difference of 90° with respect to the phase of the driving current signal were separately extracted from the signals generated in the pair of receiving coils 7 and 8 and the pair of receiving coils 12 and 13 respectively. Then, a signal ratio (V90'/V90) was determined for each of a steel sheet having a ferrite phase fraction of 100% and a steel sheet having an austenite phase fraction of 50%.

Here, in FIG. 6, for example, in the case of a steel sheet having a ferrite phase fraction of 100%, the signal ratio (V90'/V90) is measured along the vertical axis, and the distance (mm) between the steel sheet and the driving coil is measured along the horizontal axis. As illustrated in FIG. 6, it is clarified that it is possible to determine the distance between the steel sheet and the driving coil on the basis of the signal ratio. In accordance with aspects of the present invention, by using the distance between the steel sheet and the driving coil, the magnitudes of the received signals obtained by using the receiving coils 12 and 13 are corrected. By comparing the corrected signals with the magnitudes of the signal for a steel sheet having a ferrite phase fraction of 100% and the signal for a steel sheet having an austenite phase fraction of 100%, which have been determined in advance with the steel sheets being placed at the reference position, it is possible to determine the magnetic transformation rate of the steel sheet. Here, although the case of a steel sheet having a ferrite phase fraction of 100% has been described, for example, a case of a steel sheet having a ferrite phase fraction of 70% and a bainite phase fraction of 30% may appropriately be selected.

Incidentally, in the case of the present example 2, as in the case described above, the number of turns of the receiving coils connected to each other to form one pair may be different from each other. With this, since it is possible to arrange the receiving coils so that the distances of the coils from the driving coils are different from each other, it is possible to decrease the occupation volume of the apparatus 15 for measuring magnetic transformation including the receiving coils. In addition, it is possible to relax the limitation on an installation position.

In addition, in the case of 50%-γ steel, the same results as that illustrated in FIG. 6 was obtained within a tolerance of ±1%. That is, it was possible to measure a distance regardless of a γ phase fraction.

EXAMPLE 3

In the present example, the apparatus 15 for measuring magnetic transformation described in examples 1 and 2 above was used in a continuous galvanizing process. The apparatus 15 for measuring magnetic transformation was installed in the last pass of a cooling zone located on the upstream side of a galvanizing pot. In the apparatus 15 for measuring magnetic transformation, the time rate of variation in the measured magnetic transformation rate was calculated, and a variation in magnetism due to a variation in magnetic transformation rate, that is, a variation in austenite phase fraction was determined. Then, in the case where a variation in magnetism due to a variation in austenite phase fraction exceeded a predetermined threshold value, the control output was adjusted before the object portion of the steel sheet passed through the solenoid-type induction heating apparatus so that a variation in voltage was inhibited. With this, when the object portion of the steel sheet passed, since the control response speed was decreased so that an excessive variation in output power was prevented, it was possible to stably perform induction heating control. As a result, it was possible to perform heating within the target range of a variation in heating temperature.

In contrast, as a comparative example, the above-described control intervention according to aspects of the present invention on the basis of the magnetic transformation rate signal was stopped. As a result, since a portion in which a variation in austenite phase fraction exceeded the threshold value was subjected to induction heating with ordinary control, instability was generated by the excessive response of the control system, which resulted in the heating temperature exceeding the target range.

REFERENCE SIGNS LIST 1 steel sheet
2 continuous annealing furnace
3 hearth roll
4 ceramic pipe
5 coil
6 driving coil
7 receiving coil
8 receiving coil
9 transmitter
10 voltmeter
11 radiation thermometer
12 receiving coil
13 receiving coil
14 measurement processing unit
15 apparatus for measuring magnetic transformation

The invention claimed is:

1. A method for measuring a magnetic transformation rate of a steel sheet in an annealing furnace before the steel sheet is subjected to a heating treatment in the annealing furnace, by using a driving coil and receiving coils arranged on one surface side of the steel sheet so that the receiving coils are arranged on both sides of the driving coil and parallel to a surface of the steel sheet, the method comprising:
   delivering an alternating-current driving signal to the surface of the steel sheet by using an air-core driving coil having a size larger than a width of the steel sheet;
   measuring the driving signal reflected by the steel sheet by using air-core receiving coils having a size larger than the width of the steel sheet; and
   determining the magnetic transformation rate of the steel sheet by using a measurement processing unit based on a distance between the steel sheet and the driving coil which has been corrected by using the measured values of the driving signal obtained by using the receiving coils.

2. The method for measuring a magnetic transformation rate of a steel sheet in an annealing furnace according to claim 1, wherein two of the receiving coils are paired, arranged symmetrically with respect to the driving coil, connected with phases opposite to each other, and used to measure the reflected driving signal.

3. The method for measuring a magnetic transformation rate of a steel sheet in an annealing furnace according to claim 2,
   wherein two pairs of receiving coils, where each pair consists of two of the receiving coils connected with phases opposite to each other, are used and arranged so that a distance of one pair from the driving coil is different from a distance of another pair from the driving coil, and
   wherein, by using the measurement processing unit, the magnetic transformation rate is corrected based on the distances of the receiving coils from the steel sheet calculated based on the measured values of the driving signal obtained by using the two pairs of receiving coils.

4. The method for measuring a magnetic transformation rate of a steel sheet in an annealing furnace according to claim 1,
   wherein two pairs of receiving coils, where each pair consists of two of the receiving coils connected with phases opposite to each other, are used and arranged so that a distance of one pair from the driving coil is different from a distance of another pair from the driving coil, and
   wherein, by using the measurement processing unit, the magnetic transformation rate is corrected based on the distances of the receiving coils from the steel sheet calculated based on the measured values of the driving signal obtained by using the two pairs of receiving coils.

5. A continuous annealing process comprising:
   measuring a magnetic transformation rate of a steel sheet before the steel sheet enters an induction heating apparatus in an annealing furnace by using the method for measuring a magnetic transformation rate of a steel sheet in an annealing furnace according to claim 1; and
   controlling the induction heating apparatus through feedforward control based on the measured magnetic transformation rate by using the measurement processing unit.

6. A continuous galvanizing process comprising:
   measuring a magnetic transformation rate of a steel sheet before the steel sheet enters an induction heating apparatus in an annealing furnace by using the method for measuring a magnetic transformation rate of a steel sheet in an annealing furnace according to claim 1; and
   controlling the induction heating apparatus through feedforward control based on the measured magnetic transformation rate by using the measurement processing unit.

7. A method for measuring a magnetic transformation rate of a steel sheet in an annealing furnace before the steel sheet is subjected to a heating treatment in the annealing furnace, by using a driving coil and receiving coils arranged on one surface side of the steel sheet so that the receiving coils are arranged on both sides of the driving coil and parallel to a surface of the steel sheet, the method comprising:

delivering an alternating-current driving signal to the surface of the steel sheet by using an air-core driving coil having a size larger than a width of the steel sheet;

measuring the driving signal reflected by the steel sheet by using air-core receiving coils having a size larger than the width of the steel sheet; and determining the magnetic transformation rate of the steel sheet by using a measurement processing unit based on a signal component having a phase difference of 90° with respect to the delivered driving signal extracted from the measured values of the driving signal obtained by using the receiving coils.

8. The method for measuring a magnetic transformation rate of a steel sheet in an annealing furnace according to claim 7, wherein, in the measurement processing unit, each of the measured values of the driving signal obtained by using the receiving coils is separated into a signal component having a phase difference of 0° with respect to the delivered driving signal and a signal component having a phase difference of 90° with respect to the delivered driving signal, and the magnetic transformation rate is determined based on a ratio of a magnitude of the signal component having a phase difference of 90° to a magnitude of the signal component having a phase difference of 0°.

9. A continuous annealing process comprising:

measuring a magnetic transformation rate of a steel sheet before the steel sheet enters an induction heating apparatus in an annealing furnace by using the method for measuring a magnetic transformation rate of a steel sheet in an annealing furnace according to claim 7; and controlling the induction heating apparatus through feed-forward control based on the measured magnetic transformation rate by using the measurement processing unit.

10. A continuous galvanizing process comprising:

measuring a magnetic transformation rate of a steel sheet before the steel sheet enters an induction heating apparatus in an annealing furnace by using the method for measuring a magnetic transformation rate of a steel sheet in an annealing furnace according to claim 7; and controlling the induction heating apparatus through feed-forward control based on the measured magnetic transformation rate by using the measurement processing unit.

11. An apparatus for measuring a magnetic transformation rate of a steel sheet in an annealing furnace before the steel sheet is subjected to a heating treatment in the annealing furnace, by using a driving coil and receiving coils arranged on one surface side of the steel sheet so that the receiving coils are arranged on both sides of the driving coil and parallel to a surface of the steel sheet, the apparatus comprising:

an air-core driving coil which forms a large-area closed circuit having a size larger than a width of the steel sheet and delivers an alternating-current driving signal to a surface of the steel sheet;

air-core receiving coils which form large-area closed circuits having a size larger than the width of the steel sheet and receive and measure the driving signal reflected by the steel sheet; and a measurement processing unit which determines the magnetic transformation rate of the steel sheet based on a distance between the steel sheet and the driving coil which has been corrected by using the measured values of the driving signal obtained by using the receiving coils.

12. The apparatus for measuring a magnetic transformation rate of a steel sheet in an annealing furnace according to claim 11, wherein two of the receiving coils are paired, arranged symmetrically with respect to the driving coil, and connected with phases opposite to each other.

13. The apparatus for measuring a magnetic transformation rate of a steel sheet in an annealing furnace according to claim 12, wherein two pairs of receiving coils, where each pair consists of two of the receiving coils connected with phases opposite to each other, are used and arranged so that a distance of one pair from the driving coil is different from a distance of another pair from the driving coil.

14. The apparatus for measuring a magnetic transformation rate of a steel sheet in an annealing furnace according to claim 13, wherein a number of turns in a coil varies from one receiving coil to another in the receiving coils, and a distance between each of the receiving coils and the driving coil is determined in accordance with the number of turns of the receiving coil.

15. The apparatus for measuring a magnetic transformation rate of a steel sheet in an annealing furnace according to claim 12, wherein a number of turns in a coil varies from one receiving coil to another in the receiving coils, and a distance between each of the receiving coils and the driving coil is determined in accordance with the number of turns of the receiving coil.

16. The apparatus for measuring a magnetic transformation rate of a steel sheet in an annealing furnace according to claim 11, wherein two pairs of receiving coils, where each pair consists of two of the receiving coils connected with phases opposite to each other, are used and arranged so that a distance of one pair from the driving coil is different from a distance of another pair from the driving coil.

17. The apparatus for measuring a magnetic transformation rate of a steel sheet in an annealing furnace according to claim 16, wherein a number of turns in a coil varies from one receiving coil to another in the receiving coils, and a distance between each of the receiving coils and the driving coil is determined in accordance with the number of turns of the receiving coil.

18. The apparatus for measuring a magnetic transformation rate of a steel sheet in an annealing furnace according to claim 11, wherein a number of turns in a coil varies from one receiving coil to another in the receiving coils, and a distance between each of the receiving coils and the driving coil is determined in accordance with the number of turns of the receiving coil.

19. An apparatus for measuring a magnetic transformation rate of a steel sheet in an annealing furnace in which the magnetic transformation rate of a steel sheet is measured, before the steel sheet is subjected to a heating treatment in the annealing furnace, by using a driving coil and receiving coils arranged on one surface side of the steel sheet so that the receiving coils are arranged on both sides of the driving coil and parallel to a surface of the steel sheet, the apparatus comprising:

an air-core driving coil which forms a large-area closed circuit having a size larger than a width of the steel sheet and delivers an alternating-current driving signal to the surface of the steel sheet;

air-core receiving coils which form large-area closed circuits having a size larger than a width of the steel sheet and receive and measure the driving signal reflected by the steel sheet; and a measurement processing unit which determines the magnetic transformation rate of the steel sheet based on a signal component having a phase difference of 0° with respect to the delivered driving signal and/or a signal component having a phase difference of 90° with respect to the delivered driving signal which are extracted from the measured values of the driving signal obtained by using the receiving coils.

* * * * *